United States Patent [19]

Solomon et al.

[11] 4,212,742

[45] Jul. 15, 1980

[54] FILTRATION APPARATUS FOR SEPARATING BLOOD CELL-CONTAINING LIQUID SUSPENSIONS

[75] Inventors: Barry A. Solomon, Bedford; Michael J. Lysaght, Waltham, both of Mass.

[73] Assignee: United States of America, Washington, D.C.

[21] Appl. No.: 909,459

[22] Filed: May 25, 1978

[51] Int. Cl.² .............................................. B01D 31/00
[52] U.S. Cl. ................................ 210/247; 210/321 R; 210/346; 210/433 M; 210/456
[58] Field of Search ................... 210/23 F, 456, 23 H, 210/194, 321 B, 346, 195 S, 433 M, 197, 247; 260/112 B, 112 R; 424/101; 128/214 R, 214 D, 214 E, 214 C

[56] References Cited

U.S. PATENT DOCUMENTS

| | | | |
|---|---|---|---|
| 3,362,540 | 1/1968 | Bluemle, Jr. | 210/321 B |
| 3,483,867 | 12/1969 | Markovitz | 210/23 H X |
| 3,567,031 | 3/1971 | Loeffler | 210/23 F |
| 3,705,100 | 12/1972 | Blatt et al. | 210/23 F |
| 4,105,547 | 8/1978 | Sahdblom | 210/23 F X |

OTHER PUBLICATIONS

Bixler et al., "The Development of a Diatitration System for Blood Purification", from vol. XIV, Trans. Amer. Sucartle Int. Organs, 1968, pp. 99–108.
Lysaght, et al., "Development of a Microporous Membrane System for Continuous Flow Plasmapheresis", The American Society for Artificial Internal Organs, 23rd Annual Meeting, Abstract published Mar. 17, 1977, one page.

Primary Examiner—Frank A. Spear, Jr.
Attorney, Agent, or Firm—Holman & Stern

[57] ABSTRACT

A filtration device for effecting separation of a blood cell-free liquid filtrate from a blood cell-containing liquid suspension in continuous laminar flow therethrough, employing a microporous filtration membrane. The filtration flow channels along the surface of the upstream side of the membrane wall are provided with a width across the membrane wall surface which gradually and uniformly increases from the inlet end to the outlet end of the flow channel, whereby the membrane wall shear rate of the suspension in laminar flow through the flow channel will gradually and uniformly vary along the length of the flow channel from a maximum value at its inlet end to a minimum value at its outlet end. Such variation in shear rate corresponds with the variation in the transmembrane pressure conditions along the length of the flow channel so as to enable better control of the filtration operating conditions to insure optimal filtration rates per area of membrane without damage to the blood cells. Useful applications of the device include the separation of plasma from whole blood in a continuous flow plasmapheresis procedure, and the removal of cryoprotective agents from previously frozen, thawed preparations of blood cells.

7 Claims, 7 Drawing Figures

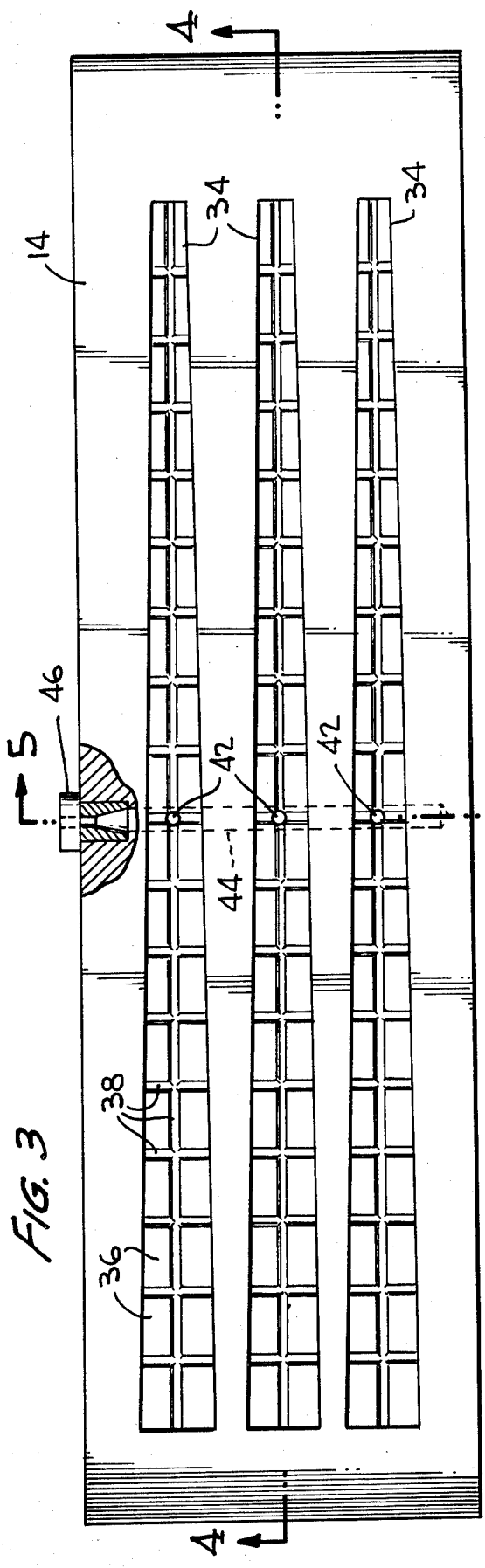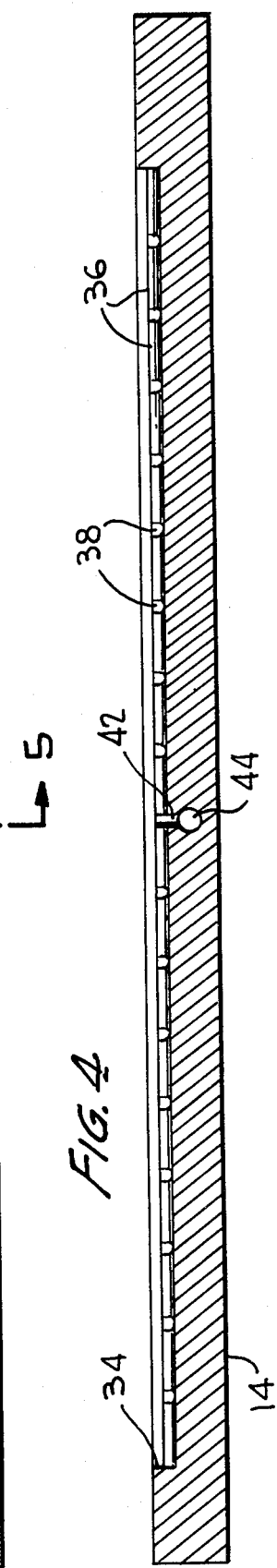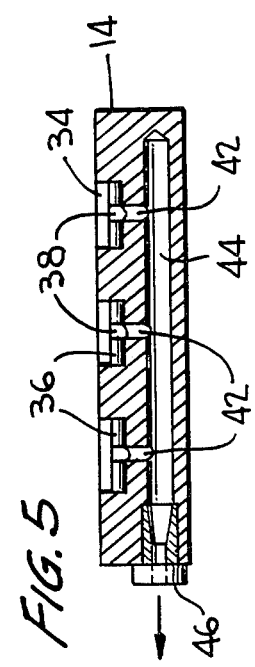

FILTRATION APPARATUS FOR SEPARATING BLOOD CELL-CONTAINING LIQUID SUSPENSIONS

The invention described herein was made in the course of work under a grant or award from the Department of Health, Education and Welfare.

BACKGROUND OF THE INVENTION

This invention relates to a fractionation of blood cell-containing liquid suspensions and, more particularly, to an apparatus for effecting such fractionation by filtration through a microporous membrane.

Certain highly desirable blood processing procedures require the ability to effect an efficient separation of a liquid suspension of blood cellular components into a cellular component-containing fraction and a cellular component-free liquid fraction without causing damage to the cellular components. For example, the preservation of red blood cells, white blood cells or platelets which have been separated from whole blood for future use in transfusions, can be effectively achieved by freezing a prepared suspension of the blood cells in an electrolyte solution containing a suitable concentration of a cryoprotective agent, such as glycerol or dimethyl sulfoxide. Since the concentration of the cryoprotective agent required for the freezing procedure is well above physiologically tolerable levels, the prepared blood cell suspension must be fractionated subsequent to thawing and prior to use so as to remove the cryoprotective agent therefrom or at least to reduce its concentration in the suspension to a physiologically tolerable level. Two techniques are currently available for effecting such fractionation, one based upon the reversible agglomeration of blood cells in the presence of carbohydrates, and the other upon various centrifugation procedures.

The problems associated with the removal of cryoprotective agents has been one of the major obstacles standing in the way of more extensive clinical use of frozen cells.

In the field of red cell freezing, various advantages have been cited for promoting the use of this product. They include a possible reduction in hepatitis transmission, a reduction in transmission of undesirable antigens and antibodies, and most important, a prolonged storage period permitting accumulation of "rare red cells" blood for autologous transfusion, and stockpiling for use during shortages. Current technology can be used to achieve these goals but a more simple and efficient system is needed.

Platelets frozen storage is desirable in order to reduce outdating and allow for provisions of "matched" or autologous cells. Techniques currently in use are not satisfactory and the microporous system may be suitable for such an application. Similarly, white cell storage is a problem and transfusion of unfrozen products are still basically experimental. However, it is expected that utilization will increase, and that frozen storage will be needed for their efficient management.

Another highly desirable blood processing procedure involving the separation of a liquid suspension of blood cellular components into a cellular component-containing fraction and a cellular component-free liquid fraction, is plasmapheresis. Plasmapheresis is defined as the process of removal of whole blood from the body of a blood donor by venesection, separation of its plasma portion, and reintroduction of the cellular portion into the donor's bloodstream. The cell-free plasma thus collected may either be used directly for patient care or further processed into specific plasma derivatives for clinical use. The return of the cellular components to the donor provides this plasma collection procedure with the advantage that it enables donations by the donor at more frequent intervals. In addition to its use for plasma collection, plasmapheresis also has therapeutic implications in plasma exchange procedures for the treatment of various clinical disorders.

Currently, the most efficient and commonly employed techniques for carrying out the plasmapheresis procedure utilize "batch" centrifugation systems for effecting the separation of the cell-free plasma from the whole blood. The most serious drawback with these currently used techniques is the relatively long period of donor time which they require, typically ranging from one to one and a half hours or more for collecting 500 ml of cell-free plasma. Such long period of donor time tends to have a detrimental effect upon the recruitment of volunteer donors and upon the overall cost-effectiveness of the plasmapheresis procedure.

Techniques for the separation of cell-free plasma from whole blood by filtration through a microporous membrane have previously been proposed. For example, in U.S. Pat. No. 3,705,100, issued Dec. 5, 1972, to Blatt et al, there is disclosed a blood fractionating process and apparatus wherein whole blood is conducted in laminar flow across the surface of a microporous membrane along a flow path which is substantially parallel to the upstream side of the membrane under pressure conditions at the inlet and outlet ends of the flow path sufficient to maintain the laminar flow and to provide a filtration driving force from the upstream side to the downstream side of the membrane. Cell-free plasma is recovered as filtrate from the downstream side of the membrane, and the cellular component-containing fraction is recovered from the outlet end of the flow path. The patent teaches that one embodiment of the process and apparatus disclosed therein is capable of separating approximately 3.0 to 3.4 ml of plasma from a 10 ml sample of fresh blood of normal hematocrit in a filtering time of 15 to 20 minutes. While such filtering capacity may be adequate for the in vitro processing of relatively small amounts of plasma for subsequent physical, chemical or clinical analyses, it obviously would not be sufficient for practical utility in plasmapheresis, where the objective is to collect 500 ml of cell-free plasma in certainly no greater and preferably substantially less than the 60 to 90 minutes required by the standard plasmapheresis techniques.

In attempting to scale up the filtration process and apparatus disclosed in the Blatt et al patent to a filtration capacity sufficient for practical utility in carrying out the plasmapheresis procedure, a number of interrelated factors must be taken into consideration. First of all, in order to minimize the total required membrane area so that the resulting filtration module will be reasonably compact in size, and in order to minimize the required period of donor time, it is most desirable to operate under conditions which will provide optimal filtrate flux, i.e., filtration rate per area of membrane. Since, in certain cases, the filtrate flux will be governed primarily by the transmembrane pressure, i.e., the pressure differential between the upstream and downstream sides of the membrane providing the filtration driving force, the transmembrane pressure should be maintained sufficiently high so as to maximize the filtrate flux. However, too high a transmembrane pressure will cause the blood cellular components to be forced to the membrane surface and interact therewith, leading to irreversible damage or hemolysis of the cells or possibly even to plugging of the membrane pores. Proper control of the transmembrane pressure so as to provide optimal filtration rate per area of membrane without causing damage to the cellular components is further complicated by the pressure drop from the inlet end to the outlet end of the blood flow path, which causes corresponding variations in the transmembrane pressure through the system. A relatively high pressure drop could lead to a very low transmembrane pressure in the outlet region. Thus, in order to insure that the transmembrane pressure in the outlet region will be maintained sufficiently high for efficient operation, the transmembrane pressure in the inlet region must be correspondingly higher so as to compensate for the pressure drop through the system. Moreover, if the system is to be used for carrying out a truly continuous flow plasmapheresis procedure wherein the cellular component-containing fraction exiting from the outlet end of the filtration flow path is directly reinfused into the donor's bloodstream, a further factor influencing the transmembrane pressure through the system is the requirement that the pressure at the outlet end of the filtration flow path be at least sufficient to overcome the sum of the return venous blood pressure and the pressure drop in the return needle and tubing assembly is an accessory blood pump is to be avoided.

An improvement in the filtration process described in the aforementioned Blatt et al patent, is described and claimed in the copending U.S. patent application of Leonard I. Friedman, Franco Castino, Michael J. Lysaght and Barry A. Solomon, filed on even date herewith U.S. Ser. No. 909,458, entitled "PROCESS FOR SEPARATING BLOOD CELL-CONTAINING LIQUID SUSPENSIONS BY FILTRATION", and incorporated herein by reference. This improvement consists of controlling the membrane wall shear rate of the suspension along the filtration flow path so that such shear rate will be sufficiently high to cause axial migration of cells and inhibit interactions of the cellular components with the membrane surface at the particular transmembrane pressure conditions employed and sufficiently low so as not to itself induce mechanical lysis or damage to the cellular components. It was found that by properly correlating the membrane wall shear rate with the particular set of transmembrane pressure conditions employed, it is possible to operate at transmembrane pressures providing optimal filtration rate per area of membrane while at the same time inhibiting lysis-causing interractions of the cellular components with the membrane surface which would otherwise occur at lower membrane wall shear rates. As disclosed in said copending Friedman, et al application, such improvement enables the filtration process to be scaled up to a filtration capacity rendering it practical for use as the blood separation technique in a continuous flow plasmapheresis system, requiring a substantially shorter period of donor time than that required by the standard centrifugal techniques conventionally employed for this purpose; and furthermore broadens the applicability of the filtration process to also render it a relatively simple, efficient and economical technique for effecting removal of cryoprotective agent from a previously frozen, thawed preparation of blood cells.

As disclosed in said copending Friedman et al application, the membrane wall shear rate of the blood cell-containing liquid suspension along the filtration flow path is a function of both the inlet suspension flow rate and the filtration flow channel dimensions, increasing with increasing flow rates and/or decreasing flow channel dimensions. Thus, once the operating membrane wall shear rate has been determined so as to properly correlated with the transmembrane pressure conditions being employed to provide optimal filtrate flux without damage to the cellular components, such shear rate can be achieved by proper coordination of the inlet suspension flow rate with the filtration flow channel dimensions.

SUMMARY OF THE INVENTIONS

It is, accordingly, a primary object of the present invention to provide an improved filtration apparatus which is specifically designed for use in effectively carrying out the improved filtration process described and claimed in the aforementioned copending Friedman et al application.

Another object of the invention is to provide a filtration apparatus in accordance with the preceding object, which facilitates correlation of the membrane wall shear rate of the liquid suspension flowing therethrough with the transmembrane pressure conditions existing therein along the entire length of the filtration flow path.

A further object of the invention is to provide a filtration apparatus in accordance with the preceding objects, which in a reasonably compact size has a filtering capacity sufficient to provide 500 ml of cell-free plasma filtrate from whole blood in approximately 30 minutes.

Still another object of the invention is to provide a filtration apparatus in accordance with the preceding objects, which in a reasonably compact size, has a filtering capacity sufficient to reduce the glycerol concentration in a unit of previously frozen, thawed glycerol-containing red blood cell preparation from a cryoprotectively effective level to a physiologically tolerable level in approximately 30 minutes.

The above and other objects are achieved in accordance with the present invention by means of a filtration apparatus designed so that the membrane wall shear rate of a blood cell-containing liquid suspension in continuous laminar flow under pressure therethrough will vary along the length of the filtration flow path in the same manner as the transmembrane pressure, i.e., from a maximum value at the inlet end of the filtration flow path to a minimum value at the outlet end thereof, thereby facilitating correlation of the membrane wall shear rate with the transmembrane pressure conditions along the entire length of the filtration flow path so as to insure optimal filtrate flux without damage to the cellular components.

The filtration apparatus in accordance with the present invention comprises a housing means provided with a suspension inlet port and a suspension outlet port, the suspension inlet port leading into the inlet end of at least one continuous suspension flow channel which extends within the housing means and terminates at its outlet end in the suspension outlet port. Each flow channel has one of its walls formed of a microporous filtration membrane disposed within the housing means, whereby the flow channel defines a filtration flow path along the surface of the upstream side of its membrane wall. The housing means is further provided with a filtrate exit port disposed on the downstream side of the membrane wall. In the improved design in accordance with the present invention, each of the flow channels has a width across the surface of its membrane wall which gradually and uniformly increases along the length thereof from its inlet end to its outlet end. Since membrane wall shear rate varies inversely with the flow channel dimensions, the membrane wall shear rate of the suspension flowing along the filtration flow path will gradually and uniformly vary along the length of the flow channel from a maximum value at its inlet end to a minimum value at its outlet end.

The filtration apparatus preferably includes a plurality of such flow channels of diverging width design in spaced parallel relation to each other across the surface of a single microporous filtration membrane, whereby spaced portions of the membrane constitute the respective membrane walls of the parallel flow channels. An inlet flow distributor means connects the respective inlet ends of the parallel flow channels to the suspension inlet port, and an outlet flow collector means connects the respect outlet ends of the parallel flow channels to the suspension outlet port. A filtrate collector means disposed on the downstream side of the membrane walls collects and conducts to the filtrate exit port the filtrate passing through the respective membrane walls of the parallel flow channels. In its preferred embodiment, the filtration apparatus includes first and second microporous filtration membranes in spaced parallel relation to each other, and first and second sets of parallel spaced flow channels disposed between the two membranes, so that spaced portions of the first membrane constitute the respective membrane walls of the parallel flow channels of the first set, and spaced portions of the second membrane constitute the respective membrane walls of the parallel flow channels of the second set.

BRIEF DESCRIPTION OF THE DRAWINGS

Other features and advantages of the present invention will be apparent from the following detailed description of preferred embodiments accompanied by the attached drawings, in which:

FIG. 3 is an enlarged top view, partly in section, of the bottom outer plate member of the filtration module shown in FIG. 2;

FIG. 4 is a sectional view of the bottom outer plate member of the filtration module taken along the line 4—4 of FIG. 3;

FIG. 5 is a sectional view of the bottom outer plate member of the filtration module taken along the line 5—5 of FIG. 3;

DESCRIPTION OF PREFERRED EMBODIMENTS

Figure 1:
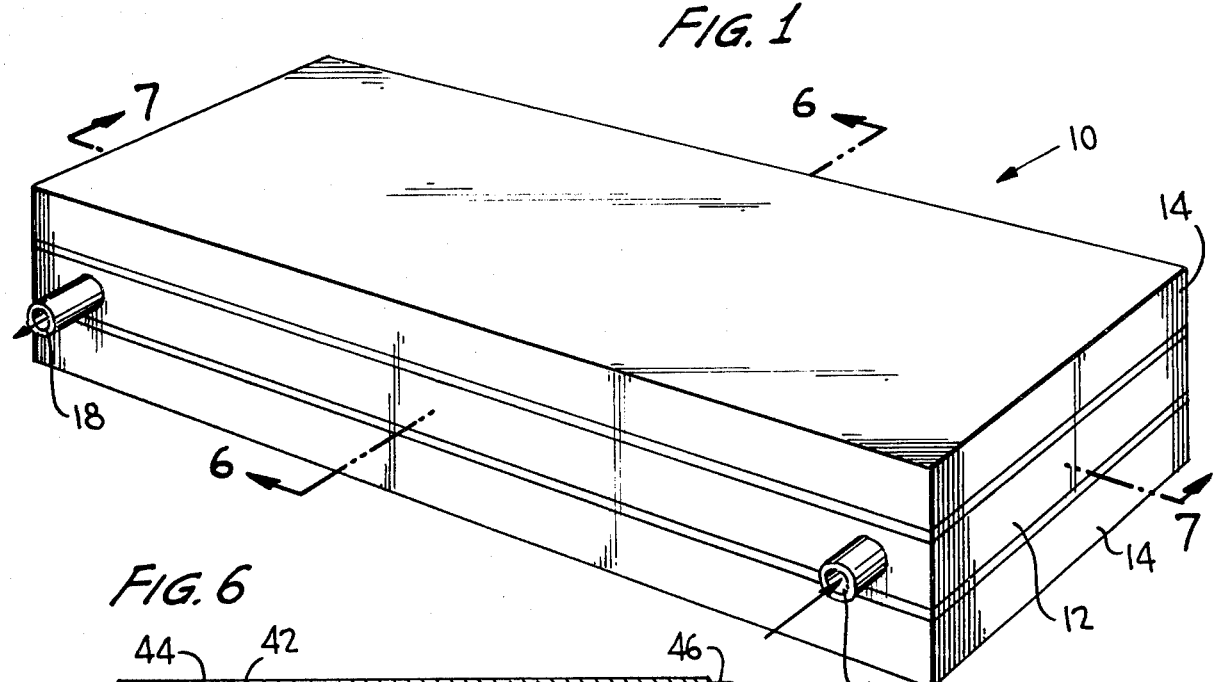
FIG. 1 is a perspective view of a filtration module designed in accordance with the present invention in its assembled form.

Referring now to FIG. 1 of the drawings, a filtration module 10 in accordance with the present invention is shown in its preferred embodiment as comprising a rectangular housing formed of a central core member 12 disposed between identical top and bottom outer plate members 14. The central core member 12 is provided at its one end with a suspension inlet port 16 leading into the housing, and at its other end with a suspension outlet port 18 leading out of the housing.

Figure 2:
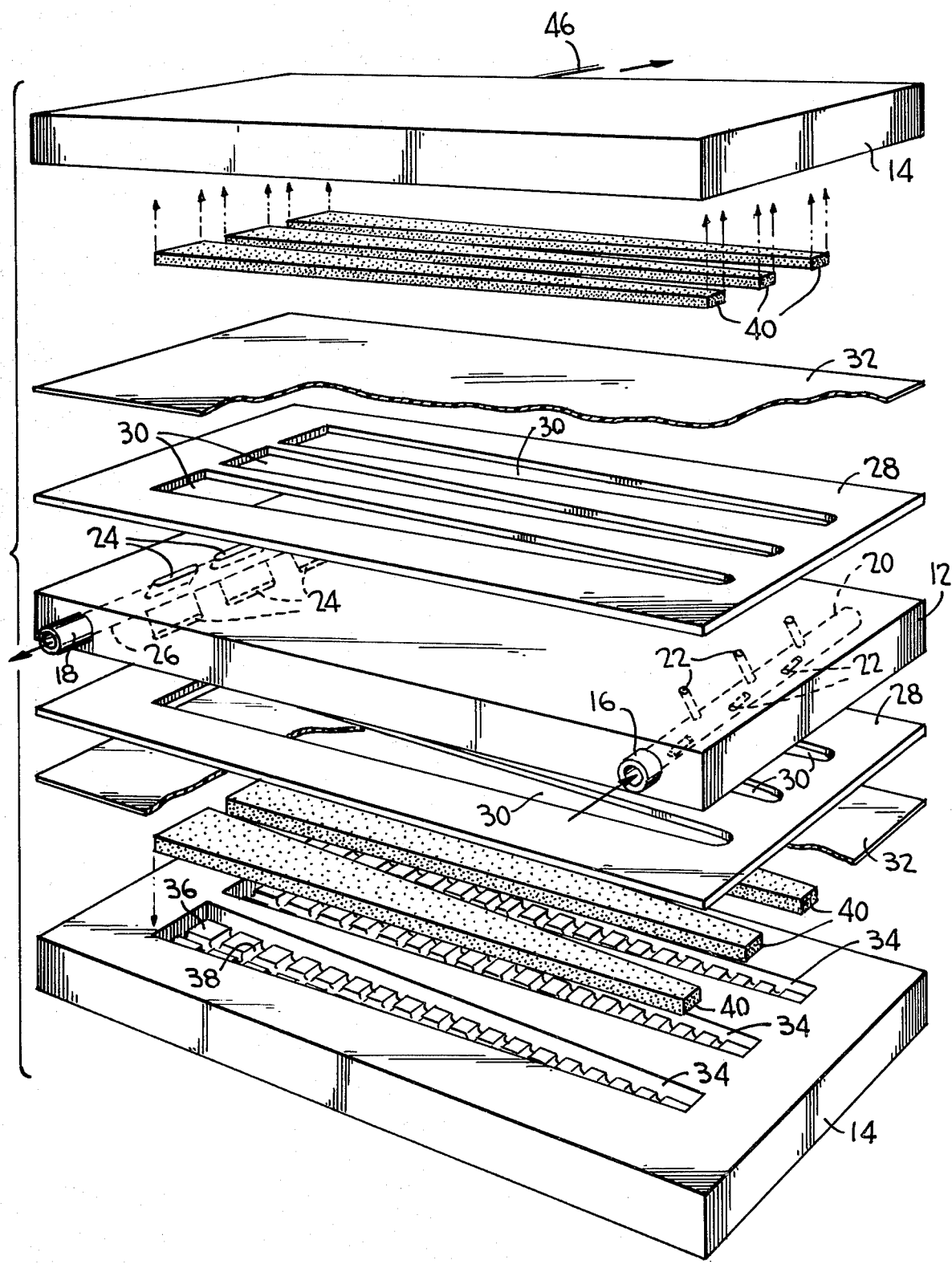
FIG. 2 is an exploded view in perspective with cut-away portions showing the component members of the filtration module of FIG. 1.

Referring now to FIG. 2, the suspension inlet port 16 is shown as leading into an inlet distributor channel 20 extending within the central core member 12 partially across its width. A plurality of inlet flow passages 22 spaced across the width of the central core member 12 lead from the inlet distributor channel 20 to the upper and lower surfaces of the central core member 12. As shown, there are six such passages 22, three leading to the upper surface and three to the lower surface of the central core member 12. At its opposite end, the central core member 12 is provided with six similarly arranged outlet flow passages 24 leading from its upper and lower surfaces into an outlet collector channel 26 which extends within the central core member 12 partially across its width and leads into the suspension outlet port 18. The outlet flow passages 24 have a wider cross section than the inlet flow passages 22.

Identical upper and lower gasket members 28 are disposed over the upper and lower surfaces, respectively, of the central core member 12. The gasket members 28 are formed of a suitable elastomeric material, such as silicone rubber, and are provided with three lengthwise extending, transversely spaced, cut-out portions 30, each of which is positioned to extend over the surface of the central core member 12 from one of the inlet flow passages 22 to the corresponding outlet flow passage 24. The width of each cut-out portion 30 gradually and uniformly increases along the length thereof from the inlet flow passage 22 to the outlet flow passage 24, its width at each end corresponding to the cross sectional width of the respective flow passage. In the preferred embodiment of the filtration module in accordance with the present invention, the ratio of the width of the cut-out portion 30 at its outlet flow passage end to that at its inlet flow passage end is approximately 2:1.

The upper and lower gasket members 28 are covered, respectively, with identical upper and lower microporous filtration membrane members 32. Such microporous membranes are known filter materials having holes of controlled shape and size running through their thickness and capable of effecting separation of very small particulate or molecular components from suspensions or solutions. Such microporous membranes are commercially available in various pore sizes. For example, polycarbonate microporous membranes are commercially available under the trademark "Nuclepore" from the Nuclepore Corporation, and cellulosic ester microporous membranes are commercially available from Millipore Corporation. Suitable pore sizes found effective for filtering cell-free plasma from whole blood or cryoprotective agent from previously frozen, thawed blood cell suspensions, range broadly from about 0.2 to about 1.5 microns in diameter, and preferably from about 0.40 to about 0.60 microns in diameter.

The upper and lower microporous filtration membrane members 32 are covered, respectively, with the top and bottom outer plate members 14 which, in their surface facing the microporous filtration membrane member, are each provided with three lengthwise extending, transversely spaced wells 34, which correspond in shape, size and relative position with the cut-out portions 30 of the gasket members 28. The bottom wall of each well 34 is provided with a plurality of flat-surfaced ridges 36 forming a network of filtrate collector grooves 38. Into each well 34 is inserted a macroporous support member 40, for example, formed of sintered polypropylene. The macroporous support members 40 are shaped and dimensioned so as to rest upon the ridges 36 of its corresponding well 34 and completely fill the well above the network of filtrate collector grooves 38.

The structure of the outer plate members 14, without the macroporous support members 40 inserted therein, is more clearly shown in FIGS. 3 to 5. The network of filtrate collector grooves 38 formed by the ridges 36 on the bottom wall of each well 34 empties through a respective filtrate flow passage 42 into a filtrate collector channel 44 which extends transversely within the outer plate member 14 midway along its length. The filtrate collector channel 44 terminates in a filtrate outlet port 46.

Figure 6:
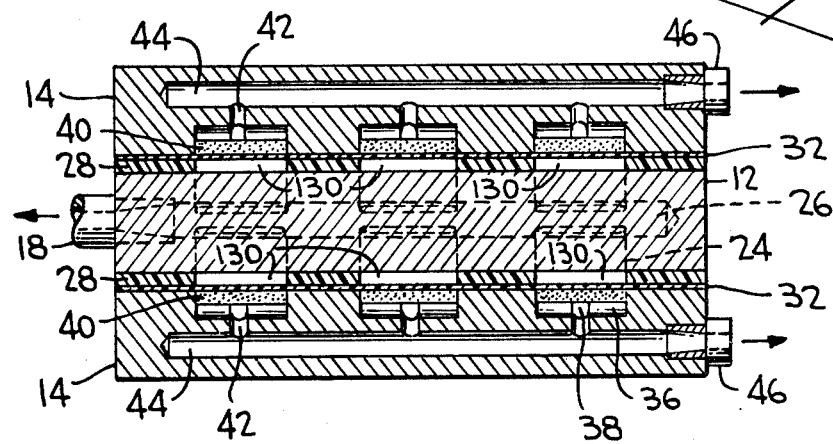
FIG. 6 is an enlarged sectional view of the assembled filtration module taken along the line 6—6 of FIG. 1.
Figure 7:
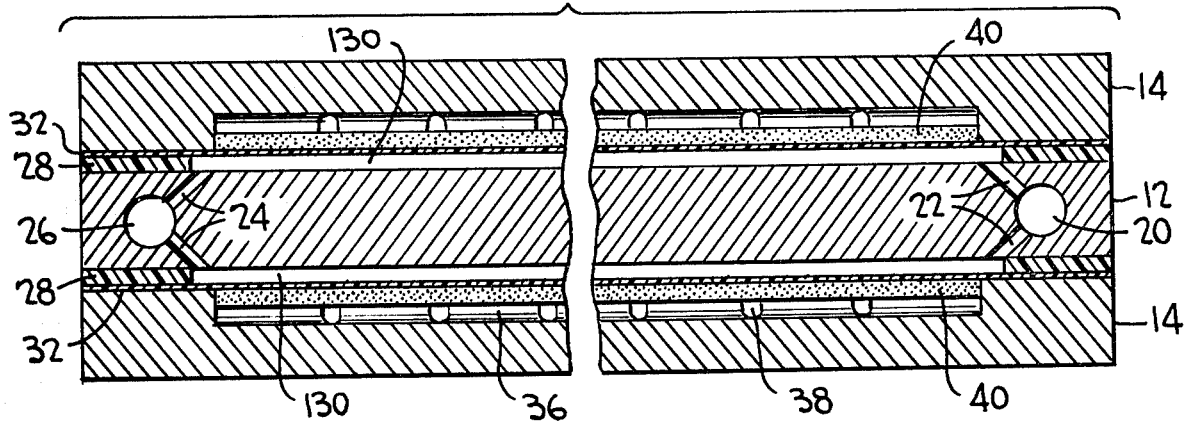
FIG. 7 is an enlarged fragmented sectional view of the assembled filtration module taken along the line 7—7 of FIG. 1.

The central core member 12, the upper and lower gasket members 28, the upper and lower microporous filtration membrane members 32, and the top and bottom outer plate members 14 with the macroporous support members 40 inserted in the wells 34 thereof, are all suitably sealed together around their peripheries so as to form the assembled filtration module 10 as shown in FIGS. 1, 6 and 7. In its assembled form, the filtration module 10 will be provided with a total of 6 spaced parallel suspension flow channels 130 arranged in upper and lower sets of three each. Each suspension flow channel 130 extends from one of the inlet flow passages 22 to the corresponding outlet flow passage 24, and is defined by a portion of the surface of the central core member 12, a portion of the surface of the upstream side of one of the microporous filtration membrane members 32, and the walls of one of the cut-out portions 30 of one of the gasket members 28. The height of the suspension flow channels 130 is determined by the thickness of the gasket members 28, and their length and width are determined by the length and width of the cut-out portions 30 of the gasket members 28. Thus, each of the suspension flow channels 130 will have a width across the surface of its membrane wall which gradually and uniformly increases along the length thereof from its inlet end to its outlet end, with the ratio of the width at the outlet end to that at the inlet end preferably being approximately 2:1.

The filtration module 10 as described above, may suitably be utilized for effecting separation of a cellular component-free liquid filtrate from a liquid suspension of blood cellular components in continuous laminar flow under pressure therethrough, such as, for example, separation of plasma from whole blood in a continuous flow plasmapheresis procedure, or removal of cryoprotective agent from a previously frozen, thawed blood cell suspension.

Details of the systems employed for carrying out these procedures are described in the copending Friedman et al application referred to above and incorporated herein by reference.

When utilizing the filtration module 10 for effecting the filtrations in procedures of the type described above, the blood cell-containing liquid suspension is pumped into the suspension inlet port 16 of the filtration module 10, and flows through the inlet distributor channel 20 and the inlet flow passages 22 into the inlet ends of the suspension flow channels 130. As the liquid suspension flows through the suspension flow channels 130, cellular component-free liquid filtrate passes through the microporous filtration membrane members 32 and the macroporous support members 40 into the network of filtrate collector grooves 38. The filtrate then drains from the network of grooves 38 through the filtrate flow passages 42 into the filtrate collector channels 44 and then out of the filtration module through the filtrate outlet ports 46. The cellular component-containing fraction of the suspension leaving the outlet ends of the suspension flow channels 130 flows through the outlet flow passages 24 into the outlet collector channel 26 and then out of the filtration module through the suspension outlet port 18.

Due to the fact that each of the suspension flow channels 130 has a width across the surface of its membrane wall which gradually and uniformly increases along the length thereof from its inlet end to its outlet end, the membrane wall shear rate of the suspension flowing along the flow channel will gradually and uniformly vary along the length of the flow channel from a maximum value at its inlet end to a minimum value at its outlet end. This corresponds with the variation in the transmembrane pressure along the length of the flow channel caused by the pressure drop through the systemn, and thereby facilitates proper correlation of the membrane wall shear rate with the transmembrane pressure conditions along the entire length of the suspension flow channel so as to insure optimal filtrate flux without damage to the cellular components.

A filtration module designed as described above was constructed with a total filtration area of 402 $cm^2$, divided evenly among its six filtration flow channels. Each channel had a height of 0.051 cm, an effective filtration length of 40.6 cm, a width of 1.1 cm at the inlet end of the filtration area and gradually and uniformly widening to 2.2 cm at the outlet end of the filtration area, and a filtration area of 67 $cm^2$. Each of the two filtration membranes employed in the filtration module was a polycarbonate microporous membrane having an average pore diameter of 0.6 microns.

The filtration module constructed as above was utilized for separating plasma from whole blood under operating conditions providing an inlet suspension flow rate into the filtration module of 270 ml/min, a transmembrane pressure of 180 mm Hg and a membrane wall shear rate of 2000 $sec^{-1}$ at the inlet end of the filtration flow channels, and a transmembrane pressure of 100 mm Hg and a membrane wall shear rate of 1000 $sec^{-1}$ at the outlet end of the filtration flow channels. The procedure resulted in the collection of 500 ml of plasma in an operating time of approximately 30 minutes. The plasma so collected was cell-free with an acceptably low level of hemoglobin content, indicating substantially hemolysis-free operation during the filtration.

The same filtration module was utilized for effecting the deglycerolization of a previously frozen, thawed preparation of red blood cells in a glycerol-containing electrolyte solution, under operating conditions providing an inlet suspension flow rate of 270 ml/min, a transmembrane pressure of 150 mm Hg and a membrane wall shear rate of 2000 $sec^{-1}$ at the inlet end of the filtration flow channels, and a transmembrane pressure of 70 mm Hg and a membrane wall shear rate of 1000 $sec^{-1}$ at the outlet end of the filtration flow channels. The procedure resulted in a reduction of the glycerol concentration in the red blood cell suspension from a cryoprotectively effective level of approximately 1.4 moles per liter to a physiologically tolerable level of about 0.1 moles per liter in a period of approximately 30 minutes. The filtrate recovered contained glycerol, was cell-free, and had a free hemoglobin concentration not significantly greater than that of the original red blood cell suspension, indicating substantially hemolysis-free operation during the filtration.

The embodiments of the invention in which an exclusive property or privilege is claimed are defined as follows:

1. In a filtration apparatus for effecting separation of a cellular component-free liquid filtrate from a liquid suspension of blood cellular components in continuous laminar flow under pressure through said apparatus by filtration through a microporous membrane which is permeable to blood proteins and impermeable to blood cellular components, comprising a housing means provided with a suspension inlet port and a suspension outlet port, said suspension inlet port leading into the inlet end of at least one continuous suspension flow channel which extends within said housing means and terminates at its outlet end in said suspension outlet port, each flow channel having one of its walls formed of a microporous filtration membrane disposed within said housing means, whereby said flow channel defines a filtration flow path along the surface of the upstream side of its membrane wall, said microporous filtration membrane being permeable to blood proteins and impermeable to blood cellular components, and said housing means being further provided with a filtrate exit port disposed on the downstream side of said membrane wall, the improvement consisting of each of said flow channels having a width across the surface of its membrane wall which gradually and uniformly increases along the length thereof from its inlet end to its outlet end, each said channel being constructed and arranged so that the membrane wall shear rate of the suspension flowing along said filtration flow path will gradually and uniformly vary along the length of said flow channel from a maximum value at said inlet end to a minimum value at said outlet end.

2. The filtration apparatus of claim 1, wherein the ratio of said width of said flow channel at its outlet end to that at its inlet end is approximately 2:1.

3. The filtration apparatus of claim 1, including a plurality of said flow channels in spaced parallel relation to each other across the surface of a single microporous filtration membrane, whereby spaced portions of said membrane constitute the respective membrane walls of said parallel flow channels.

4. The filtration apparatus of claim 3, including an inlet flow distributor means connecting the respective inlet ends of said parallel flow channels to said suspension inlet port, and an outlet flow collector means connecting the respective outlet ends of said parallel flow channels to said suspension outlet port.

5. The filtration apparatus of claim 4, including first and second microporous filtration membranes in spaced parallel relation to each other, and first and second sets of said parallel flow channels disposed between said two membranes, so that spaced portions of said first membrane constitute the respective membrane walls of said parallel flow channels of said first set, and spaced portions of said second membrane constitute the respective membrane walls of said parallel flow channels of said second set.

6. The filtration apparatus of claim 5, wherein each of said sets consists of three parallel flow channels.

7. The filtration apparatus of claim 3, including a filtrate collector means disposed on the downstream side of said membrane walls for collecting and conducting to said filtrate exit port the filtrate passing through the respective membrane walls of said parallel flow channels.

* * * * *